US012655044B2

(12) United States Patent
Subramaniam et al.

(10) Patent No.: US 12,655,044 B2
(45) Date of Patent: Jun. 16, 2026

(54) ELECTRO-ACTIVATED SUPER OXIDIZED WATER AND METHOD OF SYNTHESIZING THE SAME

(71) Applicant: Bactiguard AB, Tullinge (SE)

(72) Inventors: Sathish Komar Subramaniam, Pulau Pinang (MY); Koh Chee Keong Derick, Pulau Pinang (MY); Ranjeni Krishnen, Pulau Pinang (MY)

(73) Assignee: Bactiguard AB, Tullinge (SE)

( * ) Notice: Subject to any disclaimer, the term of this patent is extended or adjusted under 35 U.S.C. 154(b) by 261 days.

(21) Appl. No.: 18/550,187

(22) PCT Filed: Mar. 3, 2022

(86) PCT No.: PCT/MY2022/050014
§ 371 (c)(1),
(2) Date: Sep. 12, 2023

(87) PCT Pub. No.: WO2022/191697
PCT Pub. Date: Sep. 15, 2022

(65) Prior Publication Data
US 2024/0317615 A1 Sep. 26, 2024

(30) Foreign Application Priority Data

Mar. 12, 2021 (MY) .............................. PI2021001346

(51) Int. Cl.
C02F 1/32 (2023.01)
A61K 9/08 (2006.01)
(Continued)

(52) U.S. Cl.
CPC .............. C02F 1/4674 (2013.01); A61K 9/08 (2013.01); C01B 5/00 (2013.01); C02F 1/32 (2013.01);
(Continued)

(58) Field of Classification Search
CPC .. C02F 1/4674; C02F 1/32; C02F 2201/4617; C02F 2209/06; C02F 2303/04;
(Continued)

(56) References Cited

U.S. PATENT DOCUMENTS 6,719,891 B2    4/2004  Ruhr et al.
7,323,118 B2    1/2008  Calderon
(Continued)

FOREIGN PATENT DOCUMENTS

CL        2019003771 A1    4/2020
CL        2020002341 A1    11/2020
(Continued)

OTHER PUBLICATIONS

International Search Report and Written Opinion for corresponding Application No. PCT/MY2022/050014, issued on Jul. 25, 2022.
(Continued)

*Primary Examiner* — Joseph W Drodge
(74) *Attorney, Agent, or Firm* — Renner, Otto, Boisselle & Sklar, LLP

(57) ABSTRACT

The present invention relates to an electro-activated super oxidized water (EASW) which is produced on a large scale using reverse osmosis deionized water. The electro-activated super oxidized water is used an anti-microbial agent, disinfectant, and a cleaning agent in healing wounds.

3 Claims, 2 Drawing Sheets

(51) Int. Cl.

| | | |
|---|---|---|
| *C01B 5/00* | (2006.01) | |
| *C02F 1/44* | (2023.01) | |
| *C02F 1/467* | (2023.01) | |

(52) U.S. Cl.

CPC ...... *C02F 1/441* (2013.01); *C02F 2201/4617* (2013.01); *C02F 2209/06* (2013.01); *C02F 2303/04* (2013.01)

(58) Field of Classification Search

CPC .... C02F 9/00; C02F 1/22; C02F 1/441; C02F 1/66; C02F 1/44; C02F 1/4672; A01N 25/02; A01N 59/08; A01P 1/00; A61K 9/08; A61K 33/14; A61K 33/20; C01B 5/00; B01D 61/10; B01D 2311/06; B01D 2311/08; B01D 2311/106; B01D 2311/1061; B01D 2311/2684; B01D 2311/2692

See application file for complete search history.

(56) References Cited

U.S. PATENT DOCUMENTS

| | | | | |
|---|---|---|---|---|
| 10,194,665 | B2 | 2/2019 | Shichitani | |
| 2003/0034292 | A1 | 2/2003 | Rela | |
| 2003/0185704 | A1 | 10/2003 | Bernard et al. | |
| 2004/0079700 | A1* | 4/2004 | Wood | B01D 61/10 |
| | | | | 210/257.2 |
| 2005/0121334 | A1* | 6/2005 | Sumita | A61L 2/183 |
| | | | | 205/628 |
| 2005/0142157 | A1* | 6/2005 | Alimi | A61K 33/00 |
| | | | | 424/405 |
| 2006/0253060 | A1* | 11/2006 | Alimi | A61K 33/20 |
| | | | | 604/19 |
| 2006/0254930 | A1 | 11/2006 | Martinie et al. | |
| 2007/0173755 | A1* | 7/2007 | Alimi | A61K 33/20 |
| | | | | 604/29 |
| 2012/0269904 | A1* | 10/2012 | Northey | A61P 17/02 |
| | | | | 424/661 |
| 2013/0062219 | A1* | 3/2013 | Lee | B01D 61/12 |
| | | | | 205/742 |
| 2015/0119245 | A1 | 4/2015 | Robertson, Jr. et al. | |
| 2015/0231173 | A1* | 8/2015 | Sampson | A61K 9/0014 |
| | | | | 424/661 |
| 2016/0205937 | A1 | 7/2016 | Shichitani | |
| 2017/0202877 | A1* | 7/2017 | Hoover | A61K 8/891 |
| 2017/0321330 | A1* | 11/2017 | Malhotra | C25B 1/26 |
| 2019/0167717 | A1* | 6/2019 | Sampson | A23B 2/788 |
| 2020/0138953 | A1* | 5/2020 | Panicheva | A01N 25/22 |

FOREIGN PATENT DOCUMENTS

| | | | |
|---|---|---|---|
| JP | 2007517064 | A | 6/2007 |
| WO | 2006041001 | A1 | 4/2006 |
| WO | 2010027825 | A2 | 3/2010 |
| WO | 2019/178235 | A1 | 9/2019 |
| WO | 2021/095018 | A1 | 5/2021 |

OTHER PUBLICATIONS

International Preliminary Report on Patentability for corresponding Application No. PCT/MY2022/050014, issued on Dec. 30, 2022.

Yohei Takeda et al.; Acidic electrolyzed water potently inactivates SARS-CoV-2 depending on the amount of free available chlorine contacting with the virus; Biochemical and Biophysical Research Communications; Jul. 8, 2020; pp. 1-3; vol. 530.

Search Report (with English machine translation) dated Dec. 26, 2025 in related/corresponding Brazil Patent Appl. No. BR112023018319-7.

* cited by examiner

Figure 1: SPA.PH Pure Water System (RO.Ca)

1

ELECTRO-ACTIVATED SUPER OXIDIZED WATER AND METHOD OF SYNTHESIZING THE SAME

This application is a national phase of International Application No. PCT/MY2022/050014 filed Mar. 3, 2022, which claims priority to Malaysia Application No. PI2021001346 filed Mar. 12, 2021, each of which is hereby incorporated herein by reference in its entirety.

FIELD OF INVENTION

The present invention generally relates to oxidized water and particularly to electro-activated super oxidized water.

BACKGROUND OF THE INVENTION

Electrolyzed water, also known as electro-activated water or electro-chemically activated water solution, is produced by the electrolysis of ordinary tap water containing dissolved sodium chloride or other alkali metal salts. The electrolysis of such salt solution produces a solution of hypochlorous acid and sodium hydroxide. The electrolyzed water is used as a disinfectant.

For centuries, infections have been one of the critical challenges faced by millions of people globally. Infections are categorized by the types of microbes involved or source of infections that act on the hosts. Some of the deadly microbial infections infecting humans are meningitis, pneumonia, tuberculosis, botulism, anthrax, and urinary tract infections.

Further, biofilms development within chronic wounds and medical device-related infections pose a huge threat to the healthcare services which is a leading cause to patient morbidity and mortality. Up to 80% of chronic bacterial infections involve the formation of biofilms by the associated microorganisms. Generally, biofilm starts to form when the free-floating microorganisms reside on the wound or indwelling medical surface, followed by the construction of extracellular polymeric substances (EPS) that glued the bacteria and other microbial communities together, forming a three-dimensional structure. This biofilm structure act as a protective barrier to the embedded bacterial cells from any physical and chemical treatment applied. Therefore, biofilms are known to be highly resistant to antibiotics as well as immune response, leading to complications in the clinical treatment of chronic infections.

Currently, anti-biofilm strategies mainly focus on the disruption of the biofilm forming process by active anti-biofilm agents or repelling the biofilm formation through bioengineering approaches, such as the antibiofilm coatings. Despite of the existing and success of anti-biofilm technologies, patients are still at risk of developing infections in the wound. Hence, there is a need for an antiseptic solution that is effective against biofilms.

Covid-19 pandemic situation have taught us the importance of prevention mechanism in our everyday lives. Unfamiliar infectious diseases are scary. Additionally, vaccines for coronavirus are still in early stage of proving the effectiveness. Electro activated super oxidized water with established criteria have proven to be effective coronavirus (SARS-COV-2) with 99.9% reduction in 30 seconds.

The electro-activated super oxidized solution or water is produced through electrolysis process of saline water. Conventionally, electrolysis cells are only capable of generating small volumes of unstable, low pH oxidized water and the formation of hypochlorite (bleach). Hence, there is a need to develop a method of producing a large scale electro-activated super oxidized water that is more effective against microbial infections and can be used as a disinfectant or cleaning agent in wound healing.

SUMMARY OF THE INVENTION

Thus, the primary object of the present invention is to provide electro-activated super oxidized water that is effective against microbial infections.

Another object of the present invention is to provide electro-activated super oxidized water that is effective against microbial biofilms.

Yet another object of the present invention is to provide a method of producing electro-activated super oxidized water on a large scale.

Another object of the present invention is to provide electro-activated super oxidized water that is more effective against microbial infections.

Another object of the present invention is to provide electro-activated super oxidized water that can be used as a disinfectant or cleaning agent in wound healing.

Yet another object of the present invention is to provide an electro-activated super oxidized water suitable for a wide range of applications in both medical and non-medical field including terminal disinfection, drinking water sanitation, foot and wheel dips, fogging, aerial disinfection for poultry, fish farmers and general agricultural uses, hand and surface disinfectant and general disinfection for medical equipment and wound care solution.

According to the embodiments of the present invention, an electro-activated super oxidized water is provided. The electro-activated super oxidized water comprises hypochlorous acid, sodium hypochlorite (NaOCl), sodium chloride (NaCl) and purified water. The hypochlorous acid is present in an amount of 0.0002%-0.01%. The sodium hypochlorite (NaOCl) and sodium chloride (NaCl) are present in a concentration of less than equal to 0.1% while the water is present in a concentration of 99.9%.

According to an embodiment of the present invention, the electro activated super oxidized water has a pH in the range of 5.5-8.0.

According to an embodiment of the present invention, the electro activated super oxidized water comprises free available chlorine in a range of 30 ppm-500 ppm and an oxidation-reduction potential (ORP) of >850 mV.

According to an embodiment of the present invention, the electro activated super oxidized water is effective against a plurality of bacteria, wherein the plurality of bacteria includes *Escherichia coli, Bacillus cereus, Pseudomonas aeruginosa, Enterococcus faecalis, Enterococcus faecalis, Salmonella* sp., *Staphylococcus aereus, Listeria* sp., *Legionella* sp., and *Pseudomonas putida.*

According to an embodiment of the present invention, the electro activated super oxidized water is effective against a plurality of fungi, wherein the pluralFCity of fungi includes *Candida albicans, Bacilus subtilis, Clostridium difficile* and *Clostridium sporogenes.*

According to an embodiment of the present invention, the electro activated super oxidized water is effective against a plurality of spores, wherein the plurality of spores includes *Trichophytan mentagrophytes, Sporothrix schenckii, Candida auris.*

According to an embodiment of the present invention, the electro activated super oxidized water is effective against SARS-COV-2.

According to an embodiment of the present invention, a method of synthesizing electro-activated super oxidized water is provided. The method comprises electrolysing a water comprising sodium chloride in an electrolysis chamber or a Hydrogenerator using a DC current, wherein the electrolysis chamber utilises a reverse osmosis de-ionized water with pure dried vacuum salt to produce the electro-activated super oxidized water.

According to an embodiment of the present invention, a method of synthesizing electro-activated super oxidized water comprises chilling reverse osmosis (RO) water to a temperature range of 20-25° C. using a chiller (101). The chilled water is then disinfected by passing the chilled water through an Ultra-violet (UV) purifier (102). The chilled water is passed through ultrafine filter cartridge (i.e.) and UV purifier (103). The filter cartridge is of 0.45 μm and 0.2 μm size. The water is then fed into a hydrogenerator for electrolysis (104). The Hydrogenerator uses a DC current to produce the electro-activated super oxidized water. The hydrogenerator comprises at least two electrolytic cells to drive a reaction of NaCl to HOCl, wherein the two electrolytic cells are cathode and anode. The HOCl is produced in the anode cell and NaOH is produced at cathode cell. The pH of water is maintained in the range of 5.5-8.0.

According to an embodiment of the present invention, a system for producing electro-activated super oxidized water is provided. The system comprises a hydrogenerator with Reverse Osmosis De-Ionized water system, wherein the hydrogenerator comprises an electrolyser (cell) to electrically activate a solution of common salt (NaCl). The electrolyser comprises at least two chambers, wherein the two chambers are anode chamber and cathode chamber. The anode chamber and cathode chamber are separated by a diaphragm each having an electrode one positive and one negative, and wherein a DC current passes through the solution producing anolyte out of the positive chamber after the brine volume undergo treatment in the negative chamber. A neutral anolyte solution is collected from anolyte output connector is used for producing the electro activated super oxidized water (EASW).

According to another embodiment of the present invention, a system for producing electro-activated super oxidized water, comprises a hydrogenerator with Reverse Osmosis De-Ionized water system. The hydrogenerator comprises an electrolyser (cell) to electrically activate a solution of common salt (NaCl) or brine solution. The electrolyser comprises at least two chambers. The two chambers are anode chamber and cathode chamber. The anode chamber and cathode chamber are separated by a diaphragm each having an electrode one positive and one negative. A DC current passes through the solution producing anolyte out of the positive chamber after the brine volume undergo treatment in the negative chamber. A neutral anolyte solution collected from anolyte output connector is used for producing the electro activated super oxidized water (EASW). The system further comprises a pH controller and a storage tank.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

4

BRIEF DESCRIPTION OF THE DRAWINGS

Other objects, features, and advantages of the invention will be apparent from the following description when read with reference to the accompanying drawings. In the drawings, wherein like reference numerals denote corresponding parts throughout the several views:

FIG. 1A is a flow chart showing the various steps involved in the method of synthesizing electro-activated super oxidized water, according to an embodiment of the present invention.

DETAILED DESCRIPTION OF THE PREFERRED EMBODIMENTS

The present invention will now be described in detail with reference to the accompanying drawings.

The various embodiments of the present invention provide electro-activated super oxidized water. The electro-activated super oxidized water comprises hypochlorous acid, sodium hypochlorite (NaOCl), sodium chloride (NaCl) and purified water.

According to an embodiment of the present invention, the electro activated super oxidized water has a pH in the range of 5.5-8.0.

According to an embodiment of the present invention, the electro activated super oxidized water comprises free available chlorine in the range of 30 ppm-500 ppm and an oxidation-reduction potential (ORP) of >850 mV. The electro activated super oxidized water is able to kill a wide range of microorganism including bacteria, fungi and virus.

According to an embodiment of the present invention, an electro activated super oxidized water is provided. The electro activated super oxidized water is used as cleaning agent in chronic wounds.

According to an embodiment of the present invention, the electro activated super oxidized water is proven effective against biofilm and SARS-COV-2 (Coronavirus). Furthermore, the electro activated super oxidized water is applicable for disinfecting purpose apart from wound management.

According to an embodiment of the present invention, the electro activated super oxidized water acts as a bactericidal, fungicidal and sporicidal.

According to an embodiment of the present invention, the electro activated super oxidized water is effective against a plurality of bacteria, wherein the plurality of bacteria includes *Escherichia coli, Bacillus cereus, Pseudomonas aeruginosa, Enterococcus faecalis, Enterococcus faecalis, Salmonella sp., Staphylococcus aereus, Listeria sp., Legionella sp., and Pseudomonas putida.*

According to an embodiment of the present invention, the electro activated super oxidized water is effective against a plurality of fungi, wherein the plurality of fungi includes *Candida albicans, Bacilus subtilis, Clostridium difficile* and *Clostridium sporogenes.*

According to an embodiment of the present invention, the electro activated super oxidized water is effective against a plurality of spores, wherein the plurality of spores includes *Trichophytan mentagrophytes, Sporothrix schenckii, Candida auris.*

According to an embodiment of the present invention, the electro activated super oxidized water is effective against SARS-COV-2.

According to an embodiment of the present invention, a method of synthesizing electro-activated super oxidized water is provided. The method utilises an electrolysis chamber or a Hydrogenerator, wherein the electrolysis chamber utilises a reverse osmosis de-ionized water with pure dried vacuum salt to produce the electro-activated super oxidized water.

Figure 1:
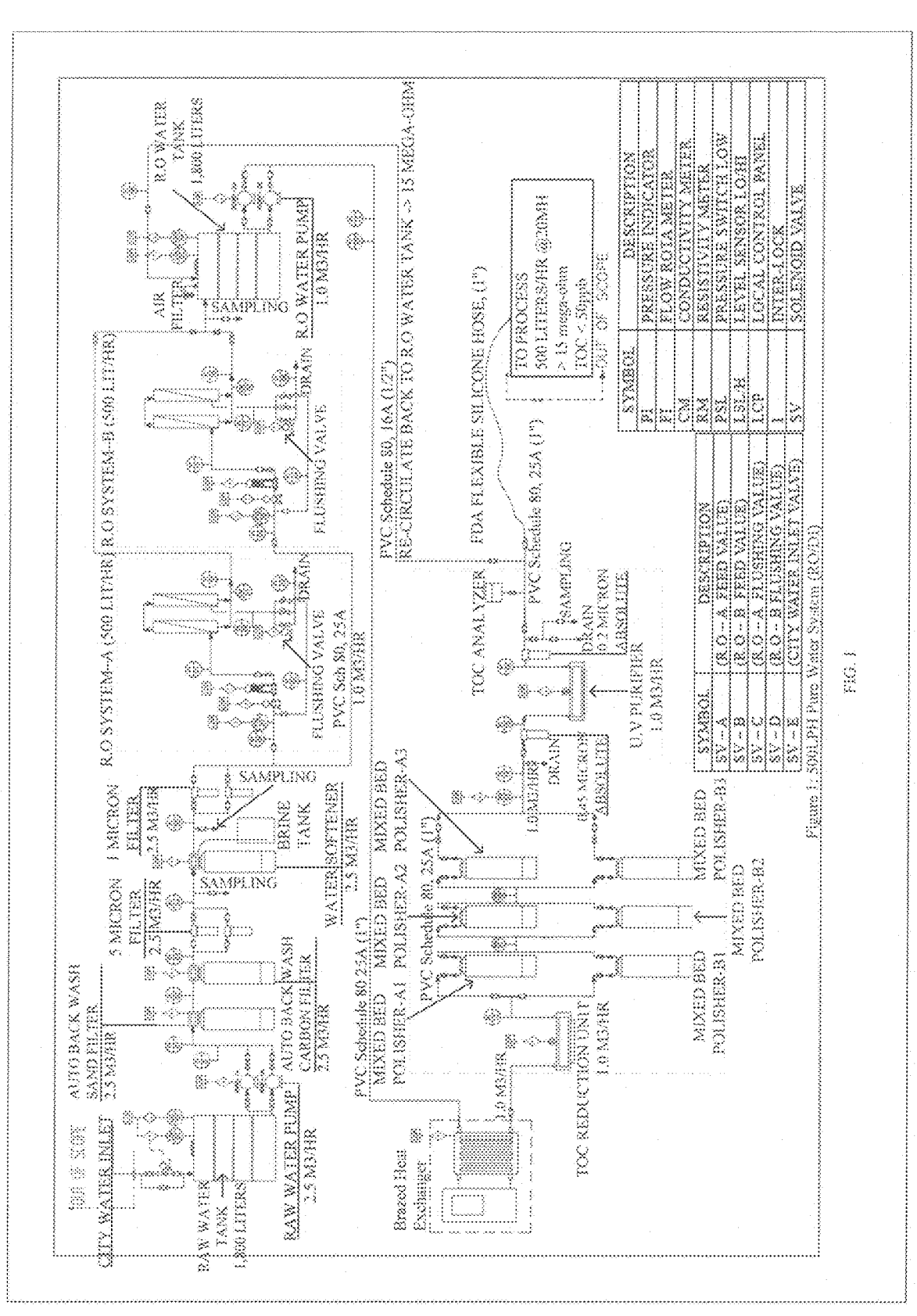
FIG. 1 shows 500 LPH Pure Water System (RO/DI), according to an embodiment of the present invention.

With respect to FIG. 1, a method of synthesizing electro-activated super oxidized water comprises chilling reverse osmosis (RO) water to a temperature range of 20-25° C. using a chiller (101). The chilled water is then disinfected by passing the chilled water through an Ultra-violet (UV) purifier (102). The chilled water is passed through ultrafine filter cartridge (i.e.) and UV purifier (103). The filter cartridge is of 0.45 μm and 0.2 μm size. The water is then fed into a hydrogenerator for electrolization (104). The Hydrogenerator uses a DC current to produce the electro-activated super oxidized water. The hydrogenerator comprises at least two electrolytic cells to drive a reaction of NaCl to HOCl, wherein the two electrolytic cell are cathode and anode. The HOCl is produced in the anode cell and NaOH is produced at cathode cell. The pH of water is maintained in the range of 5.5-8.0.

Figure 2:
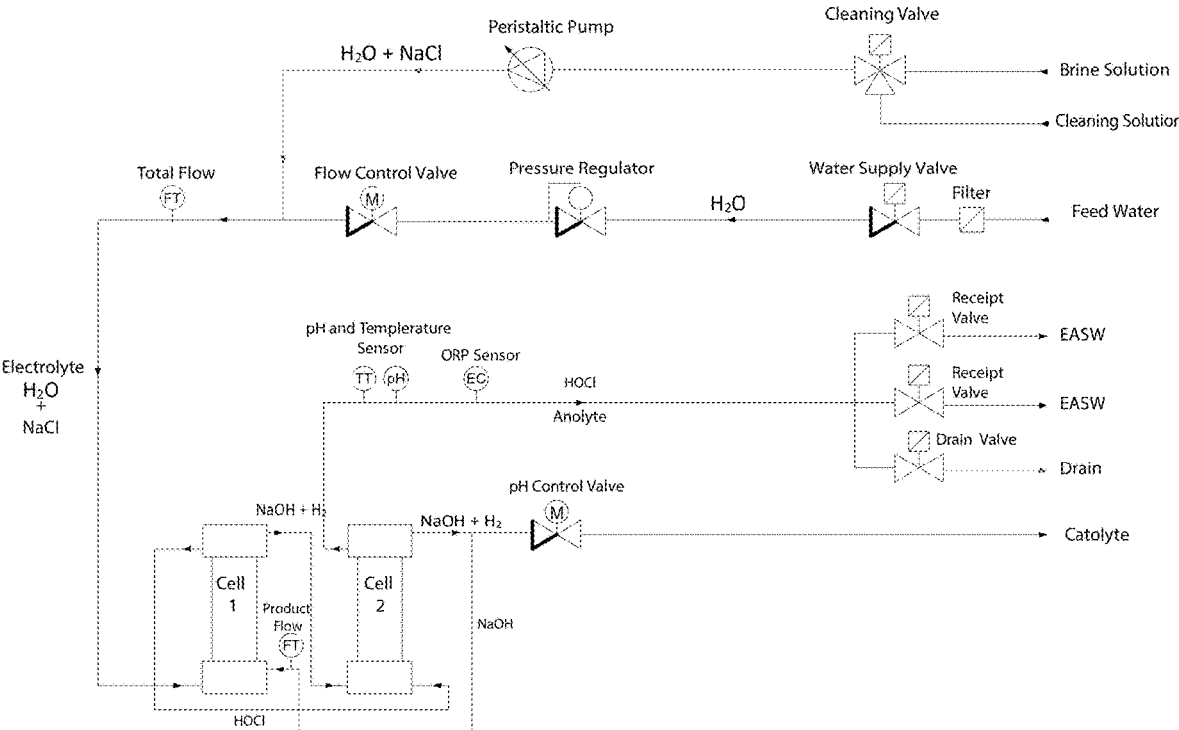
FIG. 2 shows hydrogenerator process, according to an embodiment of the present invention.

According to another embodiment of the present invention, a system for producing electro-activated super oxidized water is provided. The system comprises a hydrogenerator with Reverse Osmosis De-Ionized water system. The hydrogenerator comprises an electrolyser (cell) to electrically activate a solution of common salt (NaCl). The electrolyser comprises at least two chambers, wherein the two chambers are anode chamber and cathode chamber. The anode chamber and cathode chamber are separated by a diaphragm each having an electrode one positive and one negative. A DC current passes through the solution producing anolyte out of the positive chamber after the brine volume undergo treatment in the negative chamber. The neutral anolyte solution collected from anolyte output connector is used for the electro activated super oxidized water (EASW). FIG. 1 shows 500 LPH Pure Water System (RO/DI) and FIG. 2 shows hydrogenerator process wherein the production starts with 500 LPH Pure water system which produces pure water for electro-activated super oxidized solution production together with pure vacuum dried salt.

According to an embodiment of the present invention, reverse Osmosis De-Ionized water (RO/DI) is used to produce high quality of the solution in terms of hypochlorous acid content with less content of sodium chloride and sodium hypochlorite (ND<0.1%).

The electro-activated super oxidized water is generated by an electrolysis chamber or a Hydrogenerator. This hydrogenerator utilises a reverse osmosis de-ionized water with pure dried vacuum salt to produce the electro-activated super oxidized water.

In the process, firstly, the city water or tap water is fed into the first stage of RO/DI system, which consists of Sediment filter (mainly comprises various sizes of sands) and Carbon filter. The Sediment filter is used to trap the large free floating particles or contaminants. Whereas the Carbon filter consists of granulated carbon will absorb organics and other dissolved contaminates such as chlorine and chloramines.

After the carbon filtering stage, the water enters the softener column and the hard mineral ions (such as magnesium, $Mg_{2+}$ and calcium, $Ca_{2+}$) in the water will be removed. When the hard water enters into the mineral tank, it flows through a bed of spherical resin beads. These beads are charged with a sodium ion. The resin beads are anions with negative charge. The calcium and magnesium minerals have a positive charge, making them cations. As the hard water passes through the resin, the beads grab hold of the mineral ions and remove them from the water. When the bead seizes the mineral ion, the sodium ion is released.

Subsequently, water is fed to Reverse Osmosis (RO) system and filtered through multiple layers of thin film that remove a majority of contaminates such as salts, bacteria, heavy metals, and other organics. From here the water splits into two different water lines: the wastewater line and the product water line. The product water is almost pure and travels into the storage tank acts as a reservoir to the DI (deionization) system. Whereas certain percentage of the wastewater will be re-circulated into RO system and the remaining will be discharged to the drainage line.

Prior to feeding into DI system, the RO water will be chilled to temperature range of 20-25° C. by a chiller. The chilled water will pass through an Ultra-violet (UV) purifier to go through disinfection process. The UV purifier exposes living organisms, such as bacteria, viruses, or cysts (like *Cryptosporidium* and *Giardia*) to a germicidal ultraviolet wavelength to disrupt the DNA in pathogenic microorganisms, so they cannot reproduce.

Water after UV disinfection will pass through three identical deionizing columns consists of resin. At deionization stage, it uses an ion exchange process that attracts mineral impurities such as sodium and other metallic elements. Negatively charged Cation resin will attract positively charged ions in the water, while positively charged Anion resin attracts the negative ions. Finally, the DI water will pass through ultrafine filter cartridge (i.e. 0.45 μm and 0.2 μm) and UV purifier, then channel to Hydrogenerator.

Another important input for the EASW generation is the brine (NaCl) solution. Hydrogenerator uses aqueous solutions of NaCl to produce Anolyte and Catholyte-solution. In order to prevent the diaphragm clogging up, NaCl with the highest purity is used. The ion permeable membrane is designed to allow ions, in particular sodium and chloride ions to pass through. Using salts with a substantial amount of other ions (e.g. magnesium or calcium) that could be in the salt will result in extra cleaning of the membrane and peripheral components, and will result in a reduced lifetime.

Brine-tank ensures that the brine solution is always of the same quality. The brine-solution is always saturated, and pollution of the brine solution is avoided using an inline filter located at the bottom of the Brine-tank. The brine solution will be sucked into the Hydrogenerator from the bottom of the brine tank.

The machine uses two electrolytic cells to drive the reaction of NaCl to HOCl (product A and B) and NaOH (Catholyte). Each cell has two chambers separated by a membrane, designated by either the anode or cathode. The anode is the outer electrode, and is connected to the positive terminal of the power supply. The cathode is the inner electrode, connected to the negative terminal of the power supply. HOCl is produced in the anode chamber, and NaOH is produced in the cathode chamber. The pH/ORP probes are located in the Product A/B line (FIG. 2). It directly measures the pH/ORP of the product being produced, and is used to automatically control the pH control valve. The pH Control valve is used to control the pH of the final product. The hydrogenerator system will be operated as per validated setting to produce the desired solution. The product outlet will be connected to designated storage tank to be further filled into final bottles.

Experimental Details

An Electro Activated Super Oxidized Water (EASW) solution was developed for wound wash management. The components of the electro-activated super oxidized water are hypochlorous acid, sodium hypochlorite (NaOCl), sodium chloride (NaCl) and purified water. The EASW water has unique antimicrobial properties against wide range of pathogen due to the presence of HOCl component. Table 1 demonstrates the efficacy of EASW's ancillary antimicrobial properties, which has been evaluated as per ASTM E2315-03 (Standard Guide for Assessment of Antimicrobial Activity Using a Time-Kill Procedure).

TABLE 1

Bactericidal, Fungicidal and Sporicidal Activity of EASW

| Antimicrobial Effect | Microorganism | Microbial Presence |
|---|---|---|
| Bactericidal | *Escherichia coli* | ND (<1) |
| | *Bacillus cereus* | ND (<1) |
| | *Pseudomonas aeruginosa* | ND (<1) |
| | *Enterococcus faecalis* | ND (<1) |
| | *Salmonella* sp. | ND (<1) |
| | *Staphylococcus aereus* | ND (<1) |
| | *Listeria* sp. | ND (<1) |
| | *Legionella* sp. | ND (<1) |
| | *Pseudomonas putida* | ND(<1) |
| Fungicidal/ | *Aspergillus niger* | ND (<1) |
| Sporicidal | Yeast & mold | ND (<1) |

Table 2 shows the time duration of killing of microorganisms observed for 60 seconds of exposure of the EASW.

TABLE 2

Time-Kill Evaluation (60 sec of exposure)

| Classification | Microorganism | % Reduction |
|---|---|---|
| Bactericidal | *E. faecalis*, VRE | 99.99% |
| | MRSA | 99.99% |
| | *Mycobacterium bovis* | 99.99% |
| | *Gardnerella vaginalis* | 99.99% |
| | *Acinetobacter baumannii* | 99.99% |
| | *Klebsiella pnuemoniae* | 99.99% |
| | *Klebsiella pnuemoniae*, CRE | 99.99% |
| Fungicidal | *Candida albicans* | 99.99% |
| | *Bacilus subtilis* | 99.99% |
| | *Clostridium difficile* | 99.99% |
| | *Clostridium sporogenes* | 99.99% |
| Sporicidal | *Trichophytan mentagrophytes* | 99.99% |
| | *Sporothrix schenckii* | 99.99% |
| | *Candida auris* | 99.99% |
| Virucidal | SARS-COV-2 | 99.9% |
| | *Tested by Swedish National Veterinary Institute (SVA) | (inactivation in 30s exposure) |

Table 3 shows the anti-biofilm efficacy of the EASW.

TABLE 3

Anti-biofilm Efficacy Test

| Microbes | Result |
|---|---|
| *Pseudomonas aeruginosa* | EASW was tested against *Pseudomonas aeruginosa* biofilm. The result shows a log reduction of more than 5.95 from the initial biofilm concentration and effectively reduced biofilm by 99.9% |
| Methicillin-resistant *Staphylococcus aureus* | EASW was tested against MRSA. The result shows a log reduction of more |

TABLE 3-continued

Anti-biofilm Efficacy Test

| Microbes | Result |
|---|---|
| (MRSA) | than 4.4 from the initial biofilm concentration and is effectively reduced biofilm by 99% |

EASW has been tested for biocompatibility as per ISO 10993 and has passed following in-vivo and in vitro studies shown in Table 4.

TABLE 4 biocompatibility test

| Biocompatibility Test | Result |
|---|---|
| Acute Dermal Toxicity | No dermal toxicity |
| Intracutaneous Reactivity Irritation | No evidence of erythema or oedema |
| Primary Skin Test | No skin irritation |
| Genotoxicity | No genotoxicity effect |
| Cytotoxicity | No cytotoxic effect |
| Acute Oral Toxicity | No oral toxicity |
| Skin Sensitization Study | Non-sensitizing |
| Ocular Irritation | No ocular irritation |
| Vaginal Irritation | No vaginal irritation |
| Acute Inhalation Toxicity | No toxicity |

Electro-activated super oxidized water is being produced under the trademark Hydrocyn aqua® is suitable for a wide range of applications in both medical and non-medical field including terminal disinfection, drinking water sanitation, foot and wheel dips, fogging, aerial disinfection for poultry, fish farmers and general agricultural uses, hand and surface disinfectant and general disinfection for medical equipment and wound care solution. EASW has an efficacy that allows it to be used for nasal and oral health application which eliminated viruses that cause the common cold and influenza, as well as bacteria that causes sinusitis and oral biofilm as in table 5 below.

TABLE 5

Microorganisms affected by EASW

| Classification | Microorganism | Reduction |
|---|---|---|
| Bacteria | *Streptococcus pneumoniae* | 99.9% |
| | *Haemophilus influenzae* | 99.9% |
| | *Streptococcus pyogenes* | 99.9% |
| | *Moraxella catarrhalis* | 99.9% |
| | *Streptococcus sobrinus* | 99.9% |
| | *Streptococcus oralis* | 99.9% |
| | *Streptococcus mutans* | 99.9% |
| Virus | Rhinovirus | 99.9% |
| | Parainfluenza | 99.9% |
| | HRSV | 99.9% |
| | Adenovirus | 99.9% |
| Biofilm | *Streptococcus mutans* | 99.9% |

Additionally, EASW is also suitable for ophthalmic and respiratory care such as to be used for oxygen humidifier, replacing sterile water. Microbiological efficacy of EASW had been tested against most common infectious agents found in animal (Table 6). Test sample showed significant antimicrobial activity when tested against selected microorganisms using in vitro time kill test. This shows that the solution exhibits an effective antimicrobial activity by inhibiting growth of microorganisms. Notably, this non-antibiotic technology seems to offer a broad new paradigm for the prevention and treatment of acute and chronic skin affections in animals such as dogs. EASW is useful for Veterinary purposes for instance, solution for hot spots, scratches, skin rashes and ulcers, cuts, burns, post-surgical sites, irritated skin and lacerations for animal.

TABLE 6

| Test Result of Bactericidal and Fungicidal Activities of EASW | |
| --- | --- |
| Microorganism Species | Percent Reduction |
| *Candida albicans* | 99.999% |
| *Mycobacterium bovis* | 99.999% |
| *Staphylococcus aureus* MRSA | 99.999% |
| *Trichophyton mentagrophytes* | 99.999% |
| *Sporothrix schenckii* | 99.999% |

As will be readily apparent to those skilled in the art, the present invention may easily be produced in other specific forms without departing from its essential characteristics. The present embodiments is, therefore, to be considered as merely illustrative and not restrictive, the scope of the invention being indicated by the claims rather than the foregoing description, and all changes which come within therefore intended to be embraced therein.

The invention claimed is:

1. A method for preparing an electro-activated super oxidized aqueous composition comprising the steps of:
    providing reverse osmosis (RO) water comprising NaCl;
    chilling the reverse osmosis (RO) water to a temperature in the range of 20-25° C. using a chiller;
    disinfecting the chilled water by passing the chilled water through an ultraviolet (UV) purifier;
    passing the disinfected chilled water through an ultrafine filter cartridge and a UV purifier; and
    feeding the water to a hydrogenator for electrolyzation, wherein the hydrogenator uses a DC current to produce electro-activated super oxidized aqueous composition comprising HOCl.

2. The method as claimed in claim 1, wherein the hydrogenator comprises at least two electrolytic cells to drive a reaction of NaCl to HOCl, wherein each of the at least two electrolytic cells comprises a cathode and an anode.

3. The method as claimed in claim 2, wherein HOCl is produced at the anode of each of the at least two electrolytic cells and NaOH is produced at the cathode of each of the at least two electrolytic cells.

* * * * *